United States Patent [19]
Lok et al.

[11] Patent Number: 4,869,805
[45] Date of Patent: * Sep. 26, 1989

[54] TITANIUM-ALUMINUM-SILICON-OXIDE MOLECULAR SIEVE COMPOSITIONS

[75] Inventors: Brent M. T. Lok, New City; Bonita K. Marcus, Rye; Edith M. Flanigen, White Plains, all of N.Y.

[73] Assignee: UOP, Des Plaines, Ill.

[*] Notice: The portion of the term of this patent subsequent to Aug. 11, 2004 has been disclaimed.

[21] Appl. No.: 222,755

[22] Filed: Jul. 22, 1988

Related U.S. Application Data

[62] Division of Ser. No. 81,680, Aug. 5, 1987, Pat. No. 4,788,380, which is a division of Ser. No. 604,236, Apr. 16, 1984, Pat. No. 4,707,345.

[51] Int. Cl.$^4$ .............................................. C10G 47/02
[52] U.S. Cl. ...................................... 208/111; 208/120; 208/138; 585/266; 585/415; 585/475; 585/481; 585/514; 585/527; 585/533; 585/666; 585/667; 585/739; 585/740; 585/275
[58] Field of Search ........................ 208/111, 120, 138; 585/266, 275, 415, 481, 475, 514, 527, 533, 667, 666, 739, 740

[56] References Cited

U.S. PATENT DOCUMENTS

| | | | |
|---|---|---|---|
| 3,597,155 | 8/1971 | Flanigen | 423/328 |
| 3,941,871 | 3/1976 | Dwyer et al. | 423/326 |
| 4,310,440 | 1/1982 | Wilson et al. | 423/305 |
| 4,410,501 | 10/1983 | Taramasso et al. | 423/326 |
| 4,519,998 | 5/1985 | Leen | 423/326 |
| 4,564,511 | 1/1986 | Desmond et al. | 423/326 |
| 4,605,492 | 8/1986 | Lok et al. | 585/820 |
| 4,613,721 | 9/1986 | Kaiser | 585/514 |
| 4,684,617 | 8/1987 | Lok et al. | 423/306 |
| 4,686,029 | 8/1987 | Pellet et al. | 208/111 |
| 4,707,345 | 11/1987 | Lok et al. | 502/62 |
| 4,788,380 | 11/1988 | Lok et al. | 585/820 |

Primary Examiner—Asok Pal
Attorney, Agent, or Firm—Thomas K. McBride; Eugene I. Snyder; Frank S. Molinaro

[57] ABSTRACT

Titanium-aluminum-silicon-oxide molecular sieves are disclosed having use as molecular sieves and as catalyst compositions in hydrocarbon conversion and other processes. The molecular sieves have a unit empirical formula on an anhydrous basis of $$mR: (Ti_xAl_ySi_z)O_2$$

wherein "R" represents at least one organic+emplating agent; "m" represents the moles of "R" present per mole of $(Ti_xAl_ySi_z)O_2$; and "x", "y" and "z" represent the mole fractions of titanium, aluminum and silicon, respectively, present as tetrahedral oxides.

12 Claims, 4 Drawing Sheets

TITANIUM-ALUMINUM-SILICON-OXIDE MOLECULAR SIEVE COMPOSITIONS

This is a division of application Ser. No. 081,680 filed Aug. 5, 1987, now U.S. Pat. No. 4,788,380, which is a division of application Ser. No. 604,236, filed Apr. 16, 1984 now U.S. Pat. No. 4,707,345.

FIELD OF THE INVENTION

The present invention relates to new molecular sieve compositions containing titanium, aluminum and silicon in the form of framework tetrahedral oxide units. These compositions are prepared hydrothermally from reaction mixtures containing reactive sources of titanium, aluminum and silicon and preferably at least one organic templating agent.

DISCUSSION OF MOLECULAR SIEVES

Molecular sieves having crystalline structures and of the aluminosilicate type are well known to those familiar with molecular sieve technology. Both naturally occurring and synthetic aluminosilicates are known to exist and literally hundreds of such have been reported in the literature.

Although hundreds of aluminosilicates (binary molecular sieves) are known, the reports relating to ternary molecular sieves have been relatively few. Further, the reported ternary molecular seives having titanium as a component have been even fewer and in those instances where titanium has been reported the amount contained in the molecular sieve has been relatively small or present as a deposition or surface modifying agent.

One early report of crystalline titano-silicate zeolites (Of course, these compositions are not zeolites as the term "zeolite" is commonly employed today.) is found in U.S. Pat. No. 3,329,481. The crystalline titano-silicates are described in U.S. Pat. No. 3,329,481 by the formula:

$$(D_{2/n})_x:TiO_2(SiO_2)_y$$

wherein D is a monovalent metal, divalent metal, ammonium ion or hydrogen ion, "n" is the valence of D, "x" is a number from 0.5 to 3 and y is a number from about 1.0 to 3.5. The crystalline titano-silicate zeolites are characterized by X-ray powder diffraction patterns including all the d-spacings of one of the patterns selected from the group:

| Pattern A: | Pattern B: | Pattern C: |
| --- | --- | --- |
| 7.6 − 7.9A | 4.92 ± 0.04A | 2.82 ± 0.03A |
| 3.2 ± 0.05A | 3.10 ± 0.04A | 1.84 ± 0.03A |

The difficulty in obtaining compositions containing titanium is evidenced by the disclosure of U.S. Pat. No. 4,358,397 which discloses modified aluminosilicates. The aluminosilicates are modified by treating an aluminosilicate with a compound derived from one or more elements of titanium, zirconium or hafnium. The resulting compositions are said to contain a minor proportion of an oxide of such elements. It is clear that in the disclosed compositions the oxides of titanium, zirconium and hafnium were present as deposited oxides and were present in a minor proportion.

As above mentioned, although there has been an extensive treatment in the patent art and in the published literature of aluminosilicates and recently, aluminophosphates, there has been little information available on the presence of other than such materials. This is particularly true in the area of titanium containing compositions. Molecular sieve compositions where titanium is present in the framework of the molecular sieve or is so intimately related as to change the physical and/or chemical characteristics of the molecular sieve have not been extensively reported. This is understandable in the question of aluminosilicates, as indicated by the article, "Can $Ti^{4+}$ replace $Si^{4+}$ in silicates?". Mineralogical Magazine, September vol 37, No. 287, pages 366–369 (1969). In this article it is concluded that substitution of framework silicon by titanium does not usually occur in aluminosilicates owing to the preference of titanium to be octahedrally bound rather than tetrahedrally bound. Even for the formation of crystalline "titanosilicate zeolites*", as disclosed in U.S. Pat. No. 3,329,481 and discussed above, wherein a metallo-silicate complex is formed and treated to give the titanosilicate product, the evidence for the claimed titanosilicate is based on the X-ray powder diffraction pattern data which are somewhat suspect as to whether such show substitution of titanium into the silicate framework inasmuch as the same claimed X-ray patterns are also observed for the zirconium silicates. Further, similar X-ray patterns showing similar interplanar distances for the two values in pattern B have been reported for silicalite. (see GB 2,071,071 A).

The incorporation of titanium in a silicalite-type structure is disclosed in GB 2,071,071 A, published Dec. 21, 1979. The amount of titanium claimed to be substituted into the silicalite-type structure is very small, being no more than 0.04 mole percent, based on the number of moles of silica, and may be as low as 0.0005. The titanium content was determined by chemical analysis and was not determined to be greater than 0.023 in any of the reported examples. As indicated by a comparison of FIG. 1a and FIG. 1b of GB 2,071,071 A, the amount of titanium present is so small and no significant change in the X-ray diffraction pattern of silicalite was observed and the minor changes observed may simply be due to occluded titanium dioxide. Thus, in the absence of other analytical data the results are not well defined. No comparison data for titanium dioxide are disclosed.

In view of the above, it is clear that the substitution of titanium into a zeolitic-type framework although conceived to be possible wherein titanium substitutes for silicon, has been deemed most difficult to achieve.

The difficulty which is met in preparing titanium-containing molecular sieve compositions is further demonstrated by the failure of European patent application No. 82109451.3 (Publication No. 77,522, published Apr. 27, 1983) entitled "Titanium-containing zeolites and method for their production as well as use of said zeolites.", to actually prepare titanium-containing molecular sieve compositions. Although the applicants claim the preparation of titano-aluminosilicates having the pentasil structure, it is evident from an analysis of the prodcts of the examples that titanium was not present in the form of a framework tetrahederal oxide in a molecular sieve having the pentasil structure. The products of the examples of European patent application No. 82109451.3 will be discussed in detail in a comparative example hereinafter.

SUMMARY OF THE INVENTION

Figure 1:
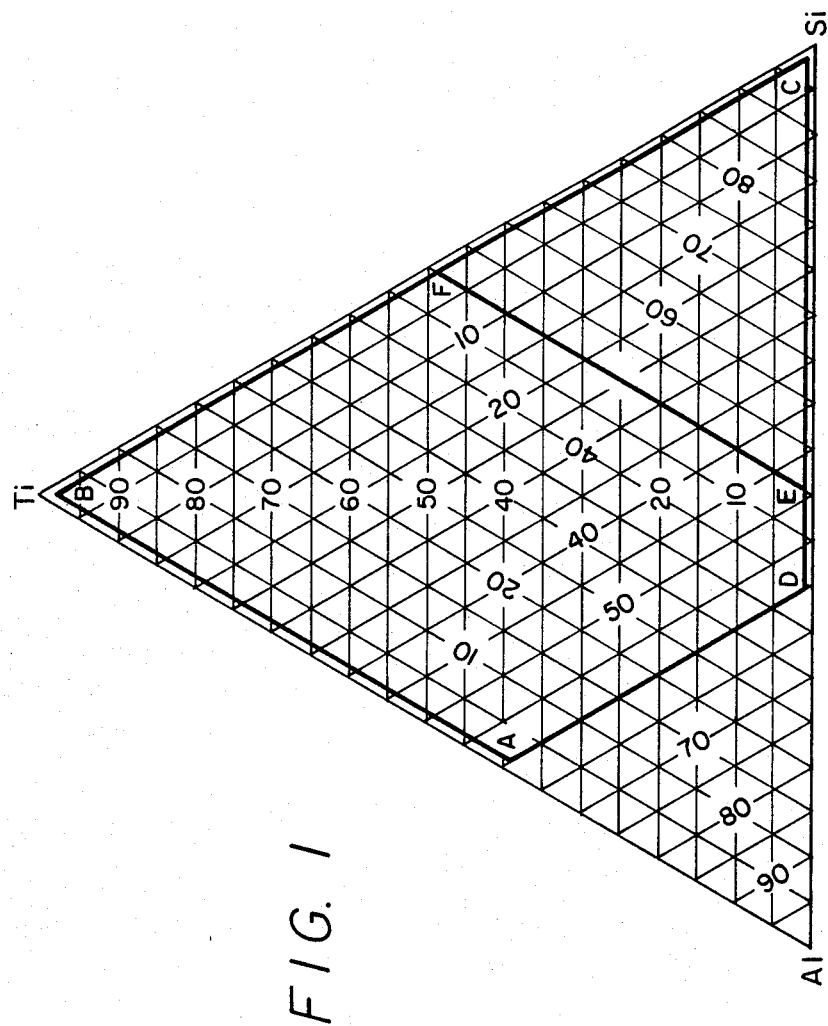
FIG. 1 is a ternary diagram wherein parameter relating to the instant compositions are set forth as mole fractions.

The instant invention relates to new molecular sieve compositions having three-dimensional microporous crystalline framework structures of $TiO_2$, $AlO_2$ and $SiO_2$ tetrahedral oxide units. These new molecular sieves have a unit empirical formula on an anhydrous basis of:

$$mR:(Ti_xAl_ySi_z)O_2$$

where "R" denominates an organic templating agent present in the intracrystalline pore system; "m" represents the moles of "R" present per mole of $(Ti_xAl_ySi_z)O_2$ and has a value of from zero to about 0.3; and "x", "y" and "z" represent the mole fractions of titanium, aluminum and silicon, respectively, present as framework tetrahedral oxide units, said mole fractions being such that they are within the area defined: by points A, B, D, E and F: or by points A, B, C and D of FIG. 1, when said molecular sieves are characterized by the X-ray patterns of tables V, VII, IX or XIV, as hereinafter defined, where points A, B, C and D have the following values for "x", "y" and "z":

| Point | Mole Fraction | | |
|---|---|---|---|
| | x | y | z |
| A | 0.39 | 0.60 | 0.01 |
| B | 0.98 | 0.01 | 0.01 |
| C | 0.01 | 0.01 | 0.98 |
| D | 0.01 | 0.60 | 0.39 |
| E | 0.01 | 0.49 | 0.50 |
| F | 0.49 | 0.01 | 0.50 | or, alternatively, "x", "y" and "z" represent mole fractions of titanium, aluminum and silicon, respectively as framework tetrahedral oxide units; said mole fractions being such that they are within the area defined by points a, b and c of FIG. 1, where points A, B, and C, have the following values for "x", "y" and "z":

| Point | Mole Fraction | | |
|---|---|---|---|
| | x | y | z |
| a | 0.49 | 0.01 | 0.50 |
| b | 0.01 | 0.49 | 0.50 |
| c | 0.01 | 0.01 | 0.98 |

The instant titanium-aluminum-silicon-oxides will be generally referred to herein by the acronym "TASO" to designate the titanium-aluminum-silicon-oxide molecular sieves having a framework structure of $TiO_2$, $AlO_2$ and $SiO_2$ tetrahedral oxide units. The individual class members or species will be identified by denominating the various structural species which make up the TASO family by assigning a number to the species and, accordingly, are identified as "TASO-i" where the number "i" is an integer. This designation is a arbitrary one and is not intended to denote structural relations to another material(s) which may also be characterized by a numbering system.

DETAILED DESCRIPTION OF THE INVENTION

Figure 2:
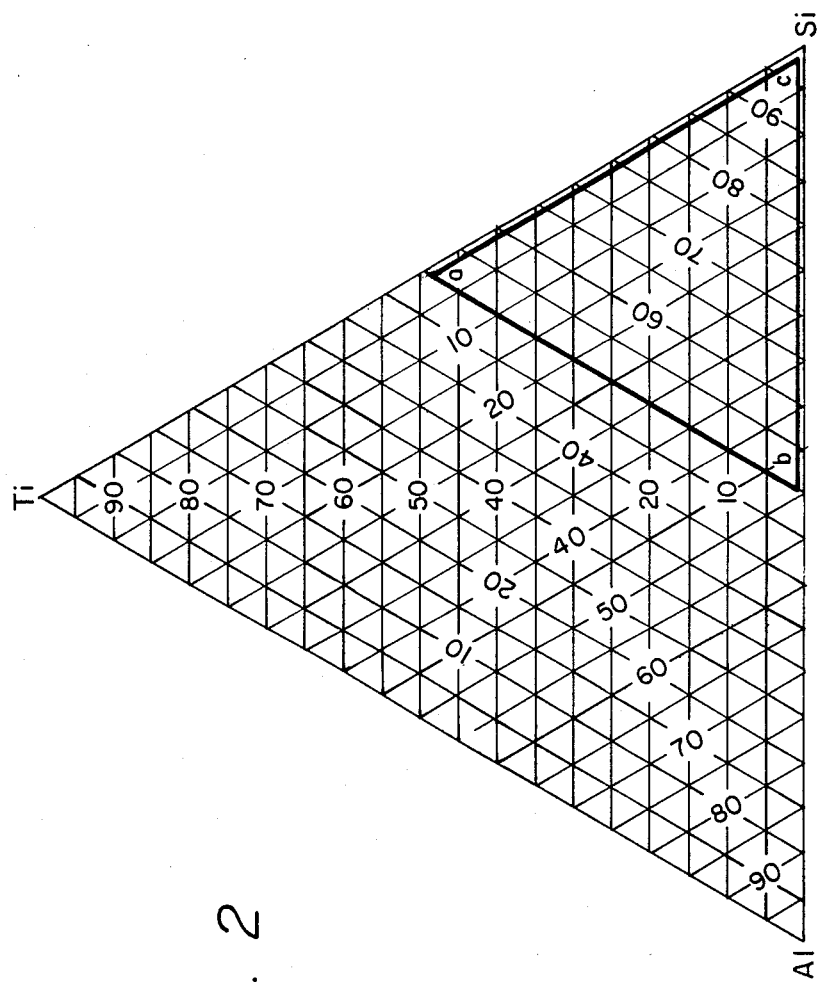
FIG. 2 is a ternary diagram wherein parameters relating to preferred compositions are set forth as mole fractions.

The present invention relates to titanium-aluminum-silicon-oxide molecular sieves having three-dimensional microporous crystal framework structures of $TiO_2$, $AlO_2$ and $SiO_2$ tetrahedral units which have a unit empirical formula on an anhydrous basis of:

$$mR:(Ti_xAl_ySi_z)O_2 \qquad (1)$$

wherein "R" represents at least one organic templating agent present in the intracrystalline pore system; "m" represents the moles of "R" present per mole of $(Ti_xAl_ySi_z)O_2$ and has a value of between zero and about 0.3, the maximum value in each case depending upon the molecular dimensions of the templating agent and the available void volume of pore system of the particular TASO molecular sieve; and "x", "y" and "y" represent the mole fractions of titanium, aluminum and silicon, respectively, present as tetrahedral oxides, said mole fractions being such that they are within the: by poinuts A, B, D, E and F; or tetragonal compositional area defined by points A, B, C and D of FIG. 1 when said molecular sieves are characterized by the X-ray patterns of Tables V, VII, IX or XVIII as hereinafter defined, and representing the following values for "x", "y" and "z":

| Point | Mole Fraction | | |
|---|---|---|---|
| | x | y | z |
| A | 0.39 | 0.60 | 0.01 |
| B | 0.98 | 0.01 | 0.01 |
| C | 0.01 | 0.01 | 0.98 |
| D | 0.01 | 0.60 | 0.39 |
| E | 0.01 | 0.49 | 0.50 |
| F | 0.49 | 0.01 | 0.50 | or, alternatively, "x", "y" and "z" represent mole fractions of titanium, aluminum and silicon, respectively as framework tetrahedral oxide units; said mole fractions being such that they are within the area defined by points a, b, and c of FIG. 2, where points a, b, and c have the following values for "x", "y" and "z":

| Point | Mole Fraction | | |
|---|---|---|---|
| | x | y | z |
| a | 0.49 | 0.01 | 0.50 |
| b | 0.01 | 0.49 | 0.59 |
| c | 0.01 | 0.01 | 0.98 |

In a further embodiment the values of "x", "y" and "z" are preferably within the compositional area defined by points A, B, D, E and F of the ternary diagram which is FIG. 1 of the drawings said points A, B, D, E and F representing the following values for "x", "y" and "z":

| Point | Mole Fraction | | |
| --- | --- | --- | --- |
| | x | y | z |
| A | 0.39 | 0.60 | 0.01 |
| B | 0.98 | 0.01 | 0.01 |
| D | 0.01 | 0.60 | 0.39 |
| E | 0.01 | 0.49 | 0.50 |
| F | 0.49 | 0.01 | 0.50 |

The molecular sieves of the present invention are generally employable as catalysts for various hydrocarbon conversion processes.

The term "unit empirical formula" is used herein according to its common meaning to designate the simplest formula which gives the relative number of moles of titanium, aluminum and silicon which form the $TiO_2$, $AlO_2$ and $SiO_2$ tetrahedral unit within a titanium-aluminum-silicon-oxide molecular sieve and which forms the molecular framework of the TASO composition(s). The unit empirical formula is given in terms of titanium, aluminum and silicon as shown in Formula (1), above, and does not include other compounds, cations or anions which may be present as a result of the preparation or the existence of other impurities or materials in the bulk composition not containing the aforementioned tetrahedral unit. The amount of template R is reported as part of the composition when the as-synthesized unit empirical formula is given, and water may also be reported unless such is defined as the anhydrous form. For convenience, coefficient "m" for template "R" is reported as a value that is normalized by dividing the number of moles of organic by the total moles of titanium, aluminum and silicon.

The unit empirical formula for a given TASO can be calculated using the chemical analysis data for that TASO. Thus, for example, in the preparation of TASOs disclosed hereinafter the over all composition of the as-synthesized TASO is calculated using the chemical analysis data and expressed in terms of molar oxide ratios on an anhydrous basis.

The unit empirical formula for a TASO may be given on an "as-synthesized" basis or may be given after an "as-synthesized" TASO composition has been subjected to some post treatment process, e.g., calcination. The term "as-synthesized" herein shall be used to refer to the TASO composition(s) formed as a result of the hydrothermal crystallization but before the TASO composition has been subjected to post treatment to remove any volatile components present therein. The actual value of "m" for a post-treated TASO will depend on several factors (including: the particular TASO, template, severity of the post-treatment in terms of its ability to remove the template from the TASO, the proposed application of the TASO composition, and etc.) and the value for "m" can be within the range of values as defined for the as-synthesized TASO compositions although such is generally less than the as-synthesized TASO unless such post-treatment process adds template to the TASO so treated. A TASO composition which is in the calcined or other post-treatment form generally has an empirical formula represented by Formula (1), except that the value of "m" is generally less than about 0.02. Under sufficiently severe post-treatment conditions, e.g. roasting in air at high temperature for long periods (over 1 hr.), the value of "m" may be zero (0) or, in any event, the template, R, is undetectable by normal analytical procedures.

The molecular sieves of the instant invention are generally synthesized by hydrothermal crystallization from a reaction mixture comprising reactive sources of titanium, aluminum and silicon, and preferably one or more templating agents. Optionally, alkali metal(s) may be present in the reaction mixture. The reaction mixture is placed in a pressure vessel, preferably lined with an inert plastic material, such as polytetrafluoroethylene, and heated, preferably under the autogenous pressure, at a temperature of from about 50° C. to about 250° C., until crystals of the molecular sieve product are obtained, usually for a period of from 2 hours to 2 weeks or more. While not essential to the synthesis of the instant molecular sieves, it has been found that in general stirring or other moderate agitation of the reaction mixture and/or seeding the reaction mixture with seed crystals of either the TASO to be produced, or a topologically similar composition, facilitates the crystallization procedure. The product is recovered by any convenient method such as centrifugation or filtration.

After crystallization the TASO may be isolated and washed with water and dried in air. As a result of the hydrothermal crystallization, the as-synthesized TASO contains within its intracrystalline pore system at least one form of any template employed in its formation. Generally, the template is a molecular species, but it is possible, steric considerations permitting, that at least some of the template is present as a charge-balancing cation. Generally the template is too large to move freely through the intracrystalline pore system of the formed TASO and may be removed by a post-treatment process, such as by calcining the TASO at temperatures of between about 200° C. and to about 700° C. so as to thermally degrade the template or by employing some other post-treatment process for removal of at least part of the template from the TASO. In some instances the pores of the TASO are sufficiently large to permit transport of the template, and, accordingly, complete or partial removal thereof can be accomplished by conventional desorption procedures such as carried out in the case of zeolites.

Figure 3:
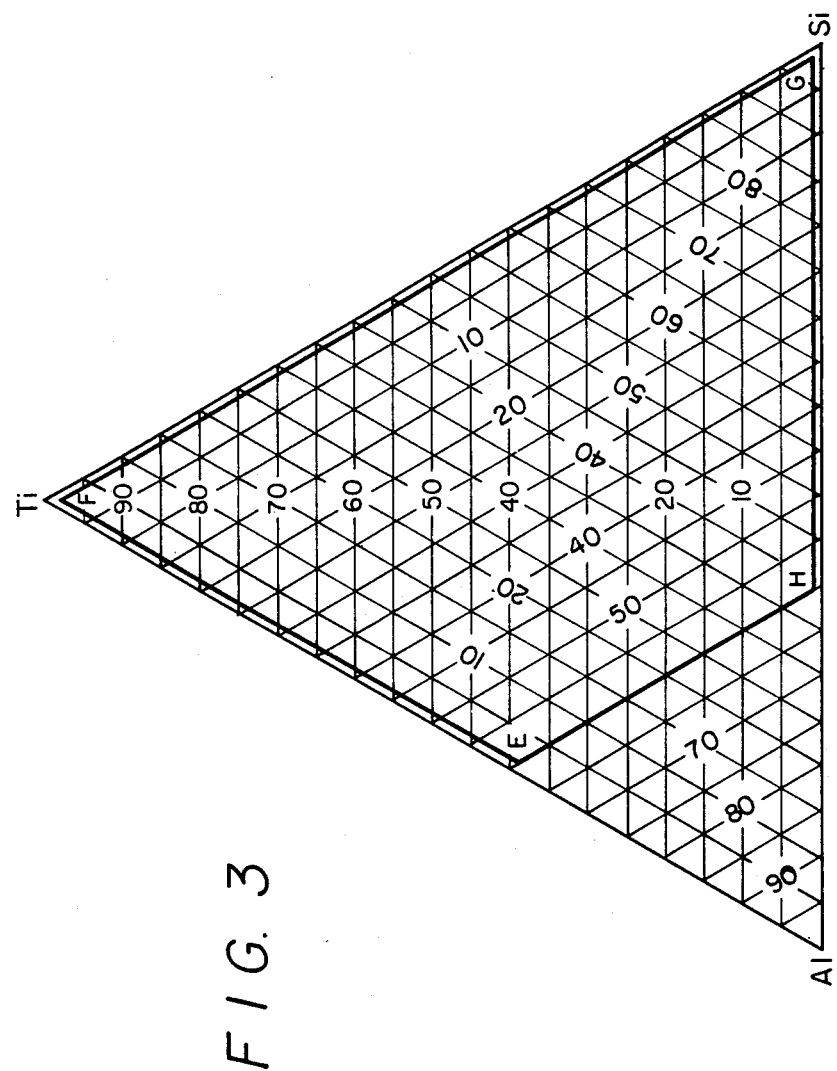
FIG. 3 is a ternary diagram wherein parameters relating to the reaction mixtures employed in the preparation of the compositions of this invention are set forth as mole fractions.

The TASO compositions are generally formed from a reaction mixture containing reactive sources of $TiO_2$, $Al_2O_3$, and $SiO_2$ and an organic templating agent, said reaction mixture comprising a composition expressed in terms of molar oxide ratios of:

wherein "R" is an organic templating agent; "a" has a value large enough to constitute an effective amount of "R" said effective amount being that amount which form said TASO compositions and preferably being from greater than zero to about 50 preferably between about 1 and about 25; "b" is an effective amount of water and has a value of from zero to about 400, preferably from about 50 to about 100; and "x", "y" and "z" represent the mole fraction, respectively of titanium, aluminum and silicon in the $(Ti_xAl_ySi_z)O_2$ constituent, and each has a value of at least 0.001 and are preferably within the tetragonal compositional area defined by points, E, F, G and H which is FIG. 3 of the drawings, said points E, F, G and H representing the following values for "x", "y" and "z":

| | Mole Fraction | | |
|---|---|---|---|
| Point | x | y | z |
| E | 0.39 | 0.60 | 0.01 |
| F | 0.98 | 0.01 | 0.01 |
| G | 0.01 | 0.01 | 0.98 |
| H | 0.01 | 0.60 | 0.39 |

The reaction mixture from which these TASOs are formed generally contain one or more organic templating agents (templates) which can be most any of those heretofore proposed for use in the synthesis of aluminosilicates and aluminophosphates. The template preferably contains at least one element of Group VA of the Periodic Table, particularly nitrogen, phosphorus, arsenic and/or antimony, more preferably nitrogen or phosphorus and most preferably nitrogen and are of the formula $R_4X^+$ wherein X is selected from the group consisting of nitrogen, phosphorus, arsenic and/or antimony and R may be hydrogen, alkyl, aryl, araalkyl, or alkylaryl group and is preferably aryl or alkyl containing between 1 and 8 carbon atoms, although more than eight carbon atoms may be present in "R" of group of the template. Nitrogen-containing templates are preferred, including amines and quaternary ammonium compounds, the latter being represented generally by the formula $R'_4N^+$ wherein each R' is an alkyl, aryl, alkylaryl, or araalkyl group; wherein R' preferably contains from 1 to 8 carbon atoms or higher when R' is alkyl and greater than 6 carbon atoms when R' is otherwise, as hereinbefore discussed. Polymeric quaternary ammonium salts such as $[(C_{14}H_{32}N_2)(OH)_2]_x$ wherein "x" has a value of at least 2 may also be employed. The mono-, di- and tri-amines, including mixed amines, may also be employed as templates either alone or in combination with a quaternary ammonium compound, quaternary phosphonium compound or another template. The exact relationship of various templates when concurrently employed is not clearly understood. Mixtures of two or more templating agents can produce either mixtures of TASOs or in the instance where one template is more strongly directing than another template the more strongly directing template may control the course of the hydrothermal crystallization wherein with the other template serving primarily to establish the pH conditions of the reaction mixture.

Representative templates which may be employed herein include: tetramethylammonium; tetraethylammonium; tetrapropylammonium; tetrabutylammonium ions; di-n-propylamine; tripropylamine; triethylamine; triethanolamine; piperidine; cyclohexylamine; 2-methylpyridine; N,N-dimethylbenzylamine; N,N-diethylethanolamine; dicyclohexylamine; N,N-dimethylethanolamine; 1,4-diazabicyclo (2,2,2) octane; N-methyldiethanolamine, N-methyl-ethanolamine; N-methylcyclohexylamine; 3-methyl-pyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. As will be readily apparent from the illustrative examples set forth hereinafter, not every template will produce every TASO composition although a single template can, with proper selection of the reaction conditions, cause the formation of different TASO compositions, and a given TASO composition can be produced using different templates.

In those instances where an alkoxide is the reactive titanium, aluminum and/or silicon source, the corresponding alcohol is necessarily present in the reaction mixture since it is a hydrolysis product of the alkoxide. It has not as yet been determined whether this alcohol participates in the synthesis process as a templating agent, or in some other function and, accordingly, is not reported as a template in the unit formula of the TASOs, although such may be acting as templates.

Alkali metal cations when present in the reaction mixture may facilitate the crystallization of certain TASO phases, although the exact function of such cations in crystallization, if any, is not presently known. Alkali cations present in the reaction mixture generally appear in the formed TASO composition, either as occluded (extraneous) cations and/or as structural cations balancing net negative charges at various sites in the crystal lattice. It should be understood that although the unit formula for the TASOs does not specifically recite the presence of alkali cations they are not excluded in the same sense that hydrogen cations and/or hydroxyl groups are not specifically provided for in the traditional formulae for zeolitic aluminosilicates.

Most any reactive titanium source may be employed herein. The preferred reactive titanium sources include titanium alkoxides, water-soluble titanates, titanate esters and titanium chelates.

Most any reactive source of silicon can be employed herein. The preferred reactive sources of silicon are silica, either as a silica sol or as fumed silica, a reactive solid amorphous precipitated silica, silica gel, alkoxides of silicon, silicic acid or alkali metal silicate and mixtures thereof.

Most any reactive aluminum source may be employed herein. The preferred reactive aluminum sources include sodium aluminate, aluminum alkoxides, such as aluminum isopropoxide, and pseudoboehmite. Crystalline or amorphous aluminosilicates which are a suitable source of silicon are, of course, also suitable sources of aluminum. Other sources of aluminum used in zeolite synthesis, such as gibbsite and aluminum trichloride may be employed but are generally not deemed preferred.

The X-ray patterns carried out herein and all other X-ray patterns appearing herein were obtained using either: (1) standard x-ray powder diffraction techniques; or (2) by use of using copper K-alpha radiation with computer based techniques using Siemens D-500 X-ray powder diffractometers, Siemens Type K-805 X-ray sources, available from Siemens Corporation, Cherry Hill, N.J., with appropriate computer interface. When employing the standard X-ray technique the radiation source is a high-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. Flat compressed powder samples are scanned at 20° (2 theta) per minute, using a two second time constant. Interplanar spacings (d) in Angstrom units are obtained from the position of the diffraction peaks expressed as $2\theta$ (theta) where theta is the Bragg angle as observed on the strip chart. Intensities are determined from the heights of diffraction peaks after subtracting background. "$I_o$" being the intensity of the strongest line or peak, and "I" being the intensity of each of the other peaks. When Relative Intensities are reported herein the following abbreviations mean:

vs=very strong; s=strong; m=medium, w=weak; and vw=very weak. Other abbreviations include: sh=shoulder and br=broad.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art.

The following examples are provided to exemplify the invention and are not meant to be limiting thereof in any way.

EXAMPLES 1-13

(a) Examples 1 to 13 were carried out to demonstrate the preparation of the TASO compositions of this invention. The TASO compositions were carried out by hydrothermal crystallization procedure discussed supra. Reaction mixtures were prepared for each example using one or more of the following preparative reagents:
(a) Tipro: Titanium isopropoxide;
(b) LUDOX-LS: Trademark of DuPont for an aqueous solution of 30 weight percent $SiO_2$ and 0.1 weight percent $Na_2O$;
(c) Sodium aluminate;
(d) Sodium hydroxide;
(e) TBABr: tetrabutylammonium bromide;
(f) TEABr: tetraethylammonium bromide; and
(g) TMAOH: tetramethylammonium hydroxide;
(i) TPABr: tetrapropylammonium bromide;

The method of addition of the above mentioned components to the reaction mixture was done according to three methods (A, B and C). Methods A, B and C are as follows:

METHOD A

Sodium hydroxide and approximately one-third of the water were blended to form a homogeneous mixture. Sodium aluminate was dissolved in this mixture and blended. LUDOX-LS was added to this mixture and the mixture blended. Titanium isopropoxide was blended into this mixture after which the organic templating agent (in approximately two-thirds of the water) was added to this mixture and blended until a homogeneous mixture was observed.

METHOD B

LUDOX-LS and titanium isopropoxide were blended to form a mixture. Sodium hydroxide was added to approximately one-half the water and then mixed with the sodium aluminate with the resulting mixture being blended until a homogeneous mixture was observed. The organic template was added to one-half the water and then added to the above mixture. The resulting mixture was blended until a homogeneous mixture was observed.

METHOD C

LUDOX-LS and one-third of the water were blended to form a homogeneous mixture. Titanium isopropoxide was added to this mixture and blended to form a homogeneous mixture. Sodium aluminate was dissolved in one-sixth of the water and blended with the above mixture. Sodium hydroxide was dissolved in one-sixth of the water and added to the above mixture and blended to provide a homogeneous mixture. The organic template (in one-third of the water) was added and the mixture again blended until a homogeneous mixture was observed.

(b) Table I sets forth the preparation of TASO-20, TASO-38, TASO-48 and TASO-49. Example A, as shown in Table I, did not contain a TASO product as indicated by X-ray analysis.

The preparative examples are identified by molar amounts of components by eR: $fAl_2O_3$:$gSiO_2$:$hTiO_2$:$iNaOH$: $jH_2O$ wherein "R" is at least one organic template as hereinbefore defined; and e, f, g, h, i and j are the number of moles of template, $Al_2O_3$, $SiO_2$, $TiO_2$, $NaOH$ and $H_2O$ respectively.

TABLE I[1]

| Example | Template | e | f | g | h | i | j | Temp (°C.) | Time (days) | Mix Method | Product[2] |
|---|---|---|---|---|---|---|---|---|---|---|---|
| 1 | TMAOH | 17 | 1.0 | 2 | 80 | 21.4 | 900 | 150 | 5 | B | TASO-20 |
| 2 | TMAOH | 17 | 1.0 | 2 | 80 | 21.4 | 900 | 150 | 12 | B | TASO-20 |
| 3 | TMAOH | 17 | 1.0 | 2 | 80 | 21.4 | 900 | 200 | 5 | B | TASO-20 |
| 4 | TMAOH | 17 | 1.0 | 2 | 80 | 21.4 | 900 | 200 | 12 | B | TASO-20 |
| 5 | TBABr | 5.6 | 0.2 | 2 | 36.8 | 8.5 | 712 | 150 | 4 | A | TASO-48 |
| 6 | TBABr | 5.6 | 0.2 | 2 | 36.8 | 8.5 | 712 | 150 | 10 | A | TASO-48 |
| 7 | TBABr | 5.6 | 0.2 | 2 | 36.8 | 8.5 | 712 | 200 | 4 | A | TASO-48 |
| 8 | TBABr | 5.6 | 0.2 | 2 | 36.8 | 8.5 | 712 | 200 | 10 | A | TASO-48 |
| 9 | TEABr | 3.8 | 0.2 | 2 | 20 | 4.2 | 210 | 150 | 10 | B | TASO-49 |
| 10 | TEABr | 3.8 | 0.2 | 2 | 20 | 4.2 | 210 | 150 | 17 | B | TASO-49 |
| 11 | TEABr | 3.8 | 0.2 | 2 | 20 | 4.2 | 210 | 150 | 24 | B | TASO-49 |
| 12 | TEABr | 3.8 | 0.2 | 2 | 20 | 4.2 | 210 | 200 | 24 | B | TASO-49 |
| 13 | TEABr | 3.6 | 1.0 | 10 | 15 | 14 | 1715 | 200 | 14 | C | TASO-38 |
| A | TPABr | 3.8 | 0.2 | 2 | 20 | 4.2 | 210 | 200 | 10 | B | — |

All amounts are given in moles
A "—" indicates that a crystalline product was not identified by X-ray analysis.

EXAMPLE 14

The TASO-48 product from example 7 was calcined and treated as hereinafter described and were then employed to determine adsorption capacities of TASO. The adsorption capacities were measured using a standard McBain-Bakr gravimetric adsorption apparatus on samples activated in a vacuum at 350° C.

The data for TASO-48, as prepared in examples 7 was as follows:

| (Example 7) TASO-48: | | | |
|---|---|---|---|
| | Kinetic Diameter, Å | Pressure (Torr) | Temp. (°C.) | wt % Adsorbed* |
| $O_2$ | 3.46 | 105 | −183 | 12.5 |
| $O_2$ | 3.46 | 747 | −183 | 13.1 |
| Cyclohexane | 6.0 | 71 | 23.5 | 0.6 |
| Neopentane | 6.2 | 750 | 23.5 | 0.6 |
| $H_2O$ | 2.65 | 4.6 | 23.5 | 3.3 |
| $H_2O$ | 2.65 | 19 | 23.4 | 6.7 |

*Calcined air at 500° C. for one hour prior to activation.

EXAMPLE 15

(a) The as-synthesized products of examples 7 and 13 were analyzed (chemical analysis) to determine the weight percent $Al_2O_3$, $SiO_2$, $TiO_2$, LOI (Loss on Ignition), carbon (C) and nitrogen (N) present as a result of the template. The results of these analyses were as follows:

| (b) (Example 7) TASO-48: | |
|---|---|
| Component | Weight Percent |
| $Al_2O_3$ | 0.73 |
| $SiO_2$ | 78.0 |
| $TiO_2$ | 5.9 |
| $Na_2O$ | 3.7 |
| C | 5.4 |
| N | 0.34 |
| LOI | 11.9 |

The above chemical analysis gives an anhydrous formula of:

$$0.0281 \text{ R } (Al_{0.010}Si_{0.936}Ti_{0.053})$$

| (c) (Example 13) TASO-38: | |
|---|---|
| Component | Weight Percent |
| $Al_2O_3$ | 4.5 |
| $SiO_2$ | 35.0 |
| $TiO_2$ | 35.1 |
| $Na_2O$ | 8.8 |
| C | 0.18 |
| N | 0.02 |
| LOI | 16.9 |

The above chemical analysis gives an anhydrous formula of:

$$0.0013 \text{ R } (Al_{0.080}Si_{0.525}Ti_{0.396})$$

EXAMPLE 16

(a) TASO-38, as referred to in example 13, was subjected to x-ray analysis. TASO-38 was determined to have a characteristic x-ray powder diffraction pattern which contains at least the d-spacing set forth in Table II below:

TABLE II

| $2\theta$ | d. (Å) | 100 × I/Io |
|---|---|---|
| 6.2 | 14.37 | 9 |
| 6.6 | 13.49 | 42 |
| 8.2 | 10.78 | 10 |
| 8.4 | 10.49 | 12 |
| 8.7 | 10.14 | 24 |
| 9.0 | 9.87 | 25 |
| 9.1 | 9.68 | 31 |
| 9.3 | 9.53 | 30 |
| 9.8 | 9.02 | 100 |
| 10.1 | 8.77 | 10 |
| 13.5 | 6.55 | 17 |
| 13.9 | 6.38 | 16 |
| 15.4 | 5.77 | 17 |
| 19.7 | 4.52 | 30 |
| 22.3 | 3.99 | 52 |
| 23.3 | 3.83 | 7 |
| 25.7 | 3.466 | 52 |
| 26.3 | 3.383 | 49 |
| 27.7 | 3.217 | 31 |
| 27.9 | 3.194 | 42 |
| 28.3 | 3.149 | 9 |
| 31.0 | 2.888 | 16 |
| 35.1 | 2.557 | 7 |
| 35.7 | 2.515 | 12 |
| 44.3 | 2.047 | 7 |
| 46.5 | 1.952 | 7 |
| 47.5 | 1.915 | 9 |
| 47.7 | 1.906 | 9 |
| 48.0 | 1.894 | 8 |
| 48.2 | 1.888 | 8 |
| 48.5 | 1.879 | 9 |
| 50.4 | 1.811 | 7 |

(b) The as-synthesized TASO-38 composition for which x-ray powder diffraction data have been obtained, including in the TASO-38 characterized by Table II, to date have patterns which are characterized by the data of Table III below:

TABLE III

| $2\theta$ | d. (Å) | 100 × I/Io |
|---|---|---|
| 6.0–6.3 | 14.75–14.12 | 7–9 |
| 6.5–6.6 | 13.67–13.49 | 20–42 |
| 8.2 | 10.78 | 12 |
| 8.4 | 10.49 | 24 |
| 8.6–8.7 | 10.33–10.14 | 9–24 |
| 9.0 | 9.87 | 25 |
| 9.1 | 9.68 | 31 |
| 9.3 | 9.53 | 30–33 |
| 9.7–9.8 | 9.12–9.02 | 100 |
| 10.1 | 8.77 | 10 |
| 13.3–13.5 | 6.66–6.55 | 10–17 |
| 13.9 | 6.38 | 8–25 |
| 15.2–15.4 | 5.82–5.77 | 17–25 |
| 19.6–19.7 | 4.53–4.52 | 30–40 |
| 22.3 | 3.99 | 49–62 |
| 23.3 | 3.83 | 7 |
| 25.3 | 3.52 | 93 |
| 25.7 | 3.466 | 52–63 |
| 26.3 | 3.383 | 40–58 |
| 27.4 | 3.255 | 14 |
| 27.7 | 3.217 | 31–33 |
| 27.8–27.9 | 3.208–3.194 | 39–51 |
| 31.0 | 2.888 | 12–20 |
| 31.5 | 2.840 | 17 |
| 35.1 | 2.557 | 7 |
| 35.7–35.8 | 2.515–2.507 | 8–13 |
| 38.0 | 2.366 | 12 |
| 44.3–44.6 | 2.047–2.038 | 7–8 |
| 45.1 | 2.009 | 7 |
| 46.5–46.6 | 1.952–1.949 | 7–9 |
| 47.5–47.6 | 1.915–1.910 | 8–9 |
| 47.7–47.9 | 1.906–1.898 | 9–10 |
| 48.0–48.1 | 1.894–1.890 | 8–25 |
| 48.2–48.5 | 1.888–1.879 | 8–13 |
| 48.5–48.6 | 1.879–1.874 | 9–13 |
| 50.4 | 1.811 | 7–13 |

(c) A portion of the as-synthesized TASO-38 of part (a) was calcined in air at 500° C. for about 1.5 hours. The calcined product was characterized by the x-ray powder diffraction pattern on Table IV, below:

TABLE IV

| $2\theta$ | d. (Å) | Relative Intensity |
|---|---|---|
| 6.6 | 13.49 | 42 |
| 8.6 | 10.33 | 17 |

TABLE IV-continued

| 2θ | d. (Å) | Relative Intensity |
|---|---|---|
| 9.0 | 9.87 | 29 |
| 9.3 | 9.53 | 33 |
| 9.8 | 9.02 | 100 |
| 13.3 | 6.66 | 10 |
| 13.9 | 6.38 | 25 |
| 15.4 | 5.77 | 22 |
| 19.7 | 4.52 | 34 |
| 22.3 | 3.99 | 62 |
| 25.7 | 3.466 | 59 |
| 26.3 | 3.383 | 58 |
| 27.9 | 3.194 | 51 |
| 31.0 | 2.887 | 20 |
| 35.7 | 2.515 | 13 |
| 46.6 | 1.949 | 9 |
| 47.9 | 1.898 | 10 |
| 48.1 | 1.890 | 14 |
| 48.4 | 1.880 | 13 |
| 48.5 | 1.879 | 13 |
| 50.4 | 1.811 | 10 |

(d) The TASO-38 compositions for which x-ray powder diffraction data have been obtained to date have patterns which are characterized by the x-ray powder diffraction pattern shown in Table V, below:

TABLE V

| 2θ | d. (Å) | 100 × I/Io |
|---|---|---|
| 9.7–9.8 | 9.12–9.02 | vs |
| 22.3 | 3.99 | m |
| 25.3 | 3.52 | vs |
| 25.7 | 3.466 | m |
| 26.3 | 3.383 | m |

EXAMPLE 17

(a) TASO-48, as referred to in example 7, was subjected to x-ray analysis. TASO-48 was determined to have a characteristic x-ray powder diffraction pattern which contains at least the d-spacings set forth in Table VI below:

TABLE VI

| 2θ | d. (Å) | 100 × I/Io |
|---|---|---|
| 5.8* | 15.24 | 10 |
| 7.8 | 11.33 | 65 |
| 8.7 | 10.16 | 40 |
| 11.8 | 7.50 | 8 |
| 13.1 | 6.76 | 8 |
| 13.8 | 6.42 | 8 |
| 14.6 | 6.07 | 13 |
| 15.2 | 5.83 | 6 |
| 15.8 | 5.61 | 10 |
| 17.1 | 5.19 | 6 |
| 17.6 | 5.04 | 6 |
| 19.1 | 4.65 | 10 |
| 20.2 | 4.40 | 15 |
| 20.7 | 4.29 | 10 |
| 21.6 | 4.11 | 10 |
| 21.9 | 4.06 | 10 |
| 22.9 | 3.88 | 100 |
| 23.7 | 3.75 | 54 |
| 24.2 | 3.68 | 23 |
| 24.5 | 3.63 | 15 |
| 25.4 | 3.507 | 10 |
| 26.4 | 3.376 | 13 |
| 26.7 | 3.339 | 13 |
| 29.0 | 3.079 | 15 |
| 29.7 | 3.008 | 17 |
| 29.9 | 2.988 | sh |
| 31.0 | 2.885 | 6 |
| 34.2 | 2.622 | 8 |
| 35.5 | 2.529 | 6 |
| 35.8 | 2.508 | 8 |
| 37.0 | 2.430 | 6 |
| 37.2 | 2.417 | 6 |
| 37.4 | 2.404 | 6 |
| 44.8 | 2.023 | 13 |
| 45.0 | 2.014 | 10 |
| 45.9 | 1.977 | 6 |
| 47.2 | 1.926 | 4 |
| 48.3 | 1.884 | 6 |
| 54.6 | 1.681 | 6 |

*Impurity Peak (b) All of the as-synthesized TASO-48 compositions for which X-ray powder diffraction data have been obtained to date have patterns which are characterized by the data of Table VII, below:

TABLE VII

| 2θ | d. (Å) | Relative Intensity |
|---|---|---|
| 7.8–8.0 | 11.33–11.05 | m–vs |
| 8.7–8.9 | 10.16–9.94 | m |
| 22.9–23.2 | 3.88–3.83 | m–vs |
| 23.7–24.0 | 3.75–3.71 | m |
| 24.2–24.4 | 3.68–3.65 | w–m |

(c) A portion of the as-synthesized TASO-48 of part (a) was calcined in air at 500° C. for about one hour. The calcined product was characterized by the X-ray powder diffraction pattern of Table VIII below:

TABLE VIII

| 2θ | d. (Å) | 100 × I/Io |
|---|---|---|
| 7.8 | 11.33 | 100 |
| 8.7 | 10.16 | 58 |
| 11.8 | 7.50 | 4 |
| 13.1 | 6.76 | 10 |
| 13.7 | 6.46 | 8 |
| 13.8 | 6.42 | 8 |
| 14.6 | 6.07 | sh |
| 14.7 | 6.03 | 17 |
| 15.4 | 5.75 | sh |
| 15.8 | 5.61 | 14 |
| 17.3 | 5.13 | 6 |
| 17.6 | 5.04 | 8 |
| 19.2 | 4.62 | 8 |
| 19.8 | 4.48 | 6 |
| 20.3 | 4.37 | 10 |
| 20.8 | 4.27 | 8 |
| 21.7 | 4.10 | 8 |
| 22.2 | 4.00 | 8 |
| 23.1 | 3.85 | 67 |
| 23.9 | 3.72 | 37 |
| 24.3 | 3.66 | 15 |
| 24.7 | 3.60 | 10 |
| 25.5 | 3.493 | 8 |
| 26.6 | 3.351 | 10 |
| 28.2 | 3.164 | 6 |
| 29.3 | 3.048 | 10 |
| 29.9 | 2.988 | 14 |
| 31.3 | 2.858 | 6 |
| 34.3 | 2.614 | 6 |
| 35.7 | 2.515 | 8 |
| 36.0 | 2.495 | 8 |
| 37.3 | 2.411 | 6 |
| 45.0 | 2.014 | 8 |
| 45.4 | 1.998 | 6 |
| 47.3 | 1.922 | 4 |
| 48.5 | 1.877 | 4 |
| 55.0 | 1.670 | 4 |

(d) The TASO-48 compositions for which X-ray powder diffraction data have been obtained to date have patterns which are characterized by the X-ray powder diffraction pattern shown in Table IX below:

TABLE IX

| 2θ | d. (Å) | 100 × I/Io |
|---|---|---|
| 7.8–8.0 | 11.33–11.05 | 65–100 |
| 8.7–8.9 | 10.16–9.94 | 35–58 |
| 11.8–11.9 | 7.50–7.44 | 2–8 |
| 13.1–13.2 | 6.76–6.71 | 5–10 |
| 13.7–13.9 | 6.46–6.37 | 4–8 |
| 14.6–14.8 | 6.07–5.99 | sh–17 |
| 15.2–15.6 | 5.83–5.68 | 3–14 |
| 15.8–15.9 | 5.61–5.57 | 7–14 |
| 17.1–17.3 | 5.19–5.13 | 3–6 |
| 17.6–17.7 | 5.04–5.01 | 6–8 |
| 19.1–19.3 | 4.65–4.60 | 3–10 |
| 19.8 | 4.48 | 6 |
| 20.2–20.4 | 4.40–4.35 | 5–15 |
| 20.7–20.9 | 4.29–4.25 | 2–10 |
| 21.6–21.7 | 4.11–4.10 | 8–10 |
| 21.9–22.2 | 4.06–4.00 | 1–10 |
| 22.9–23.2 | 3.88–3.83 | 40–100 |
| 23.7–24.0 | 3.75–3.71 | 24–54 |
| 24.2–24.4 | 3.68–3.65 | 15–23 |
| 24.5–24.7 | 3.63–3.60 | 10–15 |
| 25.4–25.6 | 3.507–3.480 | 3–15 |
| 26.4–26.7 | 3.376–3.339 | 2–13 |
| 28.1–28.2 | 3.175–3.164 | 1–6 |
| 29.0–29.3 | 3.079–3.048 | 4–15 |
| 29.7–30.0 | 3.008–2.979 | sh–17 |
| 31.0–31.3 | 2.885–2.858 | 6 |
| 34.2–34.5 | 2.622–2.600 | 2–8 |
| 35.3–35.8 | 2.543–2.508 | 1–8 |
| 36.0–36.1 | 2.495–2.488 | 2–8 |
| 37.0–37.4 | 2.430–2.404 | 1–6 |
| 44.8–45.1 | 2.023–2.010 | 5–13 |
| 45.6–45.9 | 1.989–1.977 | 3–6 |
| 47.2–47.3 | 1.926–1.922 | 4 |
| 48.3–48.7 | 1.884–1.870 | 2–6 |
| 54.4–55.0 | 1.687–1.670 | 1–6 |

EXAMPLE 18

(a) TASO-49, as referred to in example 11, was subjected to X-ray analysis and was determined to have a characteristic X-ray powder diffraction pattern which contains at least the d-spacing set forth in Table X, below:

TABLE X

| 2θ | d. (Å) | 100 × I/Io |
|---|---|---|
| 6.9 | 12.81 | sh |
| 7.3 | 12.11 | 80 |
| 7.5 | 11.79 | 67 |
| 8.6 | 10.28 | 47 |
| 18.7 | 4.75 | 40 |
| 20.6 | 4.31 | 100 |
| 22.2 | 4.00 | 53 |
| 23.0 | 3.87 | 87 |
| 25.5 | 3.493 | 47 |
| 26.2 | 3.401 | 47 |
| 26.4 | 3.376 | 47 |
| 27.8 | 3.209 | 33 |
| 38.1 | 2.362 | 20 |
| 44.3 | 2.045 | 20 |

(b) All of the TASO-49 compositions for which X-ray powder diffraction data have been obtained to date have patterns which are characterized by the data of Table XI, below:

TABLE XI

| 2θ | d. (Å) | Relative Intensity |
|---|---|---|
| 7.3–7.4 | 12.11–11.95 | m–s |
| 7.5–7.6 | 11.79–11.63 | m |
| 20.6–20.8 | 4.31–4.27 | s–vs |
| 22.2–22.3 | 4.00–3.99 | m |
| 23.0–23.1 | 3.87–3.85 | s–vs |

(c) The TASO-49 compositions for which X-ray powder diffraction data have been obtained to date have patterns which are characterized by the X-ray powder diffraction pattern shown in Table XII below:

TABLE XII

| 2θ | d. (Å) | 100 × I/Io |
|---|---|---|
| 6.9 | 12.81 | sh–20 |
| 7.3–7.4 | 12.11–11.95 | 74–80 |
| 7.5–7.6 | 11.79–11.63 | 67–75 |
| 8.6–8.9 | 10.28–9.94 | 35–47 |
| 18.7–18.8 | 4.75–4.72 | 21–40 |
| 19.0–19.1 | 4.67–4.65 | 10–20 |
| 20.6–20.8 | 4.31–4.27 | 89–100 |
| 22.2–22.3 | 4.00–3.99 | 21–53 |
| 23.0–23.1 | 3.87–3.85 | 87–100 |
| 25.5–25.6 | 3.493–3.480 | 17–47 |
| 26.2–26.3 | 3.401–3.389 | 33–47 |
| 26.4–26.5 | 3.376–3.363 | 30–47 |
| 27.8–27.9 | 3.209–3.198 | 14–33 |
| 38.0–38.1 | 2.368–2.362 | 3–20 |
| 44.3–44.4 | 2.045–2.040 | 2–20 |

EXAMPLE 19

This is a comparative example wherein example 1 of European Patent Application No. 82109451.3 was repeated and the product evaluated by several techniques as hereinafter discussed:

(a) Example 1 of European Patent Application No. 82109451.3 was repeated with the starting reaction mixture having a composition based on molar ratios of: 1 $Al_2O_3$:47 $SiO_2$:1.32 $TiO_2$:11.7 NaOH:28 TPAOH:1498-$H_2O$ The reaction mixture was divided and placed in two digestion vessels. At the end of the procedure set forth in example 1 of the European Application a sample of the product from each digestion vessel was analyzed and gave the following chemical analyses:

| | Weight Percent | |
|---|---|---|
| | Sample 1 | Sample 2 |
| $SiO_2$ | 75.3 | 75.9 |
| $Al_2O_3$ | 3.02 | 2.58 |
| $TiO_2$ | 3.91 | 4.16 |
| $Na_2O$ | 3.66 | 3.46 |
| Carbon | 6.3 | 6.7 |
| Nitrogen | 0.62 | 0.65 |
| LOI* | 14.0 | 14.0 |

*Loss on ignition

Figure 4:
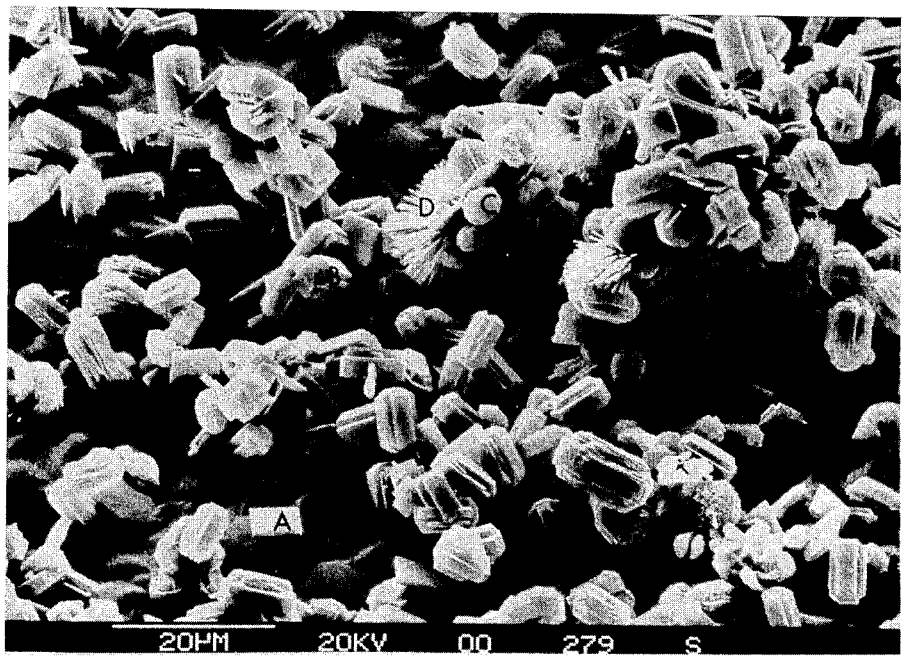
FIG. 4 is an SEM (Scanning Electron Micrograph) of the product of European application No. 82109451.3.

The two samples were then analyzed by SEM (scanning electron microscope) and EDAX (energy dispersive analysis by X-ray) micropiope. The SEM probe of the two samples showed four morphologies to be present and such are shown in FIG. 4. The four morphologies of the two samples prepared in accordance with the European application and the EDAX microprobe analysis for each was as follows:

(1) Smooth, intergrown hexagonal particles (B in FIG. 4) which are associated with a ZSM-5 morphology had an EDAX microprobe of:

| | Average of Spot Probes |
|---|---|
| Ti | 0 |
| Si | 1.0 |
| Al | 0.05 |

(2) Flat, smooth plates (A in FIG. 4) had an EDAX microprobe of:

| Average of Spot Probes | |
|---|---|
| Ti | 0.13 |
| Si | 1.0 |
| Al | 0.05 |

(3) Spheres and elongated bundles (C in FIG. 4) had an EDAX microprobe of:

| Average of Spot Probes | |
|---|---|
| Ti | 0.22 |
| Si | 1.0 |
| Al | 0.05 |
| Na | 0.10 |

(4) Needles or fine rods (D in FIG. 4) had an EDAX microprobe of:

| Average of Spot Probes | |
|---|---|
| Ti | 0.05 |
| Si | 0.8 |
| Al | 0.13 |
| Na | 0.05 |
| Cl | 0.10 |

The above SEM and EDAX data demonstrate that although ZSN-5 type crystals were formed that these crystals contained no detectable titanium. The only detectable titanium was present as impurity phases and not in crystals having the ZSM-5 structure.

The X-ray diffraction patterns of the as-synthesized materials were obtained and the following X-ray patterns were observed:

| TABLE XIII (Sample 1) | |
|---|---|
| 5.577 | 15.8467 |
| 5.950 | 14.8540 |
| 6.041 | 14.6293 |
| 6.535 | 13.5251 |
| 7.154 | 12.3567 |
| 7.895 | 11.1978 |
| 8.798 | 10.0504 |
| 9.028 | 9.7946 |
| 9.784 | 9.0401 |
| 11.846 | 7.4708 |
| 12.453 | 7.1079 |
| 12.725 | 6.9565 |
| 13.161 | 6.7267 |
| 13.875 | 6.3821 |
| 14.637 | 6.0518 |
| 14.710 | 6.0219 |
| 15.461 | 5.7310 |
| 15.881 | 5.5802 |
| 16.471 | 5.3818 |
| 17.218 | 5.1498 |
| 17.695 | 5.0120 |
| 19.212 | 4.6198 |
| 19.898 | 4.4619 |
| 20.045 | 4.4295 |
| 20.288 | 4.3770 |
| 20.806 | 4.2692 |
| 21.681 | 4.0988 |
| 22.143 | 4.0145 |
| 23.091 | 3.8516 |
| 23.641 | 3.7632 |
| 23.879 | 3.7263 |
| 24.346 | 3.6559 |
| 24.649 | 3.6116 |
| 25.548 | 3.4865 |
| 25.828 | 3.4494 |
| 26.228 | 3.3976 |
| 26.608 | 3.3501 |
| 26.887 | 3.3158 |
| 27.422 | 3.2524 |
| 28.048 | 3.1812 |
| 28.356 | 3.1473 |
| 29.191 | 3.0592 |
| 29.912 | 2.9870 |
| 30.295 | 2.9502 |
| 32.736 | 2.7356 |
| 33.362 | 2.6857 |
| 34.355 | 2.6102 |
| 34.640 | 2.5894 |
| 34.887 | 2.5716 |
| 35.152 | 2.5529 |
| 35.551 | 2.5252 |
| 35.660 | 2.5177 |
| 36.031 | 2.4926 |
| 37.193 | 2.4174 |
| 37.493 | 2.3987 |
| 45.066 | 2.0116 |
| 45.378 | 1.9985 |
| 46.514 | 1.9523 |
| 47.393 | 1.9182 |

| TABLE XIV (Sample 2) | |
|---|---|
| 5.801 | 15.2353 |
| 6.012 | 14.7012 |
| 6.169 | 14.3265 |
| 7.970 | 11.0926 |
| 8.875 | 9.9636 |
| 9.118 | 9.6981 |
| 9.879 | 8.9532 |
| 11.933 | 7.4163 |
| 12.537 | 7.0605 |
| 12.808 | 6.9115 |
| 13.242 | 6.6860 |
| 13.957 | 6.3452 |
| 14.718 | 6.0186 |
| 14.810 | 5.9813 |
| 15.542 | 5.7014 |
| 15.954 | 5.5551 |
| 16.563 | 5.3521 |
| 17.316 | 5.1211 |
| 17.788 | 4.9862 |
| 19.291 | 4.6009 |
| 20.119 | 4.4134 |
| 20.382 | 4.3571 |
| 20.879 | 4.2544 |
| 21.735 | 4.0887 |
| 22.220 | 4.0007 |
| 23.170 | 3.8387 |
| 23.730 | 3.7494 |
| 23.964 | 3.7133 |
| 24.425 | 3.6442 |
| 24.722 | 3.6011 |
| 25.900 | 3.4399 |
| 26.734 | 3.3345 |
| 26.979 | 3.3047 |
| 27.251 | 3.2724 |
| 27.494 | 3.2440 |
| 28.175 | 3.1671 |
| 28.450 | 3.1371 |
| 29.287 | 3.0493 |
| 29.970 | 2.9814 |
| 30.371 | 2.9430 |
| 30.694 | 2.9127 |
| 31.312 | 2.8566 |
| 32.825 | 2.7283 |
| 33.457 | 2.6782 |
| 34.426 | 2.6051 |
| 34.723 | 2.5834 |
| 34.879 | 2.5722 |
| 35.709 | 2.5143 |
| 36.125 | 2.4863 |
| 37.248 | 2.4139 |
| 37.490 | 2.3988 |
| 45.156 | 2.0078 |
| 45.453 | 1.9954 |

TABLE XIV (Sample 2) -continued

| | |
|---|---|
| 46.462 | 1.9544 |
| 46.608 | 1.9486 |

Table XIII and XIV shows an X-ray pattern typical of a ZSM-5 type product and can be attributed to the smooth, integrown hexagonal particles which contained no titanium. The X-ray patterns of Tables VI and VII show three peaks ($2\theta = 5.6-5.8$, 12.45-12.54 and 24.5-24.72) which could not be explained. The two samples were calcined according to the conditions set forth in the European application with a portion of both samples being calcined at 540° C. for sixteen hours. The X-ray patterns of the calcined samples were as follows.

Table XV (Sample 1)

| | |
|---|---|
| 6.141 | 14.3908 |
| 6.255 | 14.1303 |
| 8.011 | 11.0355 |
| 8.913 | 9.9209 |
| 9.144 | 9.6705 |
| 9.930 | 8.9068 |
| 11.979 | 7.3876 |
| 12.440 | 7.1152 |
| 13.289 | 6.6625 |
| 14.007 | 6.3224 |
| 14.874 | 5.9557 |
| 15.613 | 5.6757 |
| 15.995 | 5.5408 |
| 16.609 | 5.3373 |
| 17.353 | 5.1103 |
| 17.884 | 4.9597 |
| 19.335 | 4.5905 |
| 20.177 | 4.4008 |
| 20.463 | 4.3401 |
| 20.940 | 4.2422 |
| 21.845 | 4.0685 |
| 22.291 | 3.9880 |
| 23.186 | 3.8361 |
| 23.362 | 3.8076 |
| 23.817 | 3.7359 |
| 24.031 | 3.7031 |
| 24.510 | 3.6317 |
| 24.908 | 3.5747 |
| 25.699 | 3.4664 |
| 25.969 | 3.4309 |
| 26.371 | 3.3796 |
| 26.698 | 3.3389 |
| 27.022 | 3.2996 |
| 27.487 | 3.2449 |
| 28.184 | 3.1662 |
| 28.513 | 3.1303 |
| 29.369 | 3.0411 |
| 30.017 | 2.9769 |
| 30.468 | 2.9338 |
| 31.333 | 2.8548 |
| 32.877 | 2.7241 |
| 34.490 | 2.6003 |
| 35.062 | 2.5592 |
| 35.800 | 2.5082 |
| 36.186 | 2.4823 |
| 37.324 | 2.4092 |
| 37.654 | 2.3888 |
| 45.195 | 2.0062 |
| 45.631 | 1.9880 |
| 46.639 | 1.9474 |
| 47.547 | 1.9123 |
| 48.765 | 1.8674 |

Table XVI (Sample 2)

| | |
|---|---|
| 6.092 | 14.5084 |
| 6.295 | 14.0403 |
| 7.941 | 11.1328 |
| 8.838 | 10.0054 |
| 9.857 | 8.9730 |
| 11.921 | 7.4236 |
| 12.399 | 7.1383 |
| 13.222 | 6.6959 |
| 13.937 | 6.3539 |
| 14.811 | 5.9809 |
| 15.535 | 5.7038 |
| 15.916 | 5.5681 |
| 16.532 | 5.3620 |
| 17.262 | 5.1370 |
| 17.806 | 4.9811 |
| 19.268 | 4.6064 |
| 20.107 | 4.4160 |
| 20.389 | 4.3556 |
| 20.868 | 4.2567 |
| 21.807 | 4.0754 |
| 22.197 | 4.0047 |
| 23.116 | 3.8476 |
| 23.263 | 3.8235 |
| 23.755 | 3.7455 |
| 23.955 | 3.7147 |
| 24.432 | 3.6433 |
| 24.854 | 3.5823 |
| 25.653 | 3.4725 |
| 25.901 | 3.4398 |
| 26.265 | 3.3929 |
| 26.648 | 3.3451 |
| 26.976 | 3.3052 |
| 27.386 | 3.2566 |
| 28.156 | 3.1692 |
| 28.495 | 3.1323 |
| 29.304 | 3.0476 |
| 29.969 | 2.9815 |
| 30.384 | 2.9417 |
| 31.283 | 2.8592 |
| 32.819 | 2.7289 |
| 34.423 | 2.6052 |
| 34.993 | 2.5641 |
| 35.716 | 2.5138 |
| 36.146 | 2.4850 |
| 37.295 | 2.4110 |
| 37.562 | 2.3944 |
| 45.137 | 2.0086 |
| 45.523 | 1.9925 |
| 46.562 | 1.9504 |
| 47.509 | 1.9137 |

The X-ray diffraction pattern of the calcined samples shown a ZSM-5 type pattern with only slight differences from the as-synthesized. When chemical analysis (bulk) of a portion of the calcined samples 1 and 2 are carried out the following is obtained:

| | Weight Percent | |
|---|---|---|
| | Sample 1 | Sample 2 |
| $SiO_2$ | 79.6 | 81.2 |
| $Al_2O_3$ | 3.5 | 2.9 |
| $Na_2O$ | 4.4 | 4.1 |
| $TiO_2$ | 4.4 | 4.6 |
| Carbon | 0.11 | 0.10 |
| LOI* | 8.1 | 7.6 |

*Loss on Ignition

When the molar ratio of oxides is computed for the above bulk analysis the following is obtained:

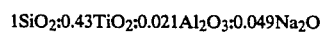

This compares quite well with the bulk chemical analysis reported in the European application which is:

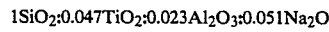

It is clear that the product crystals which gave the product an X-ray pattern characteristic of ZSM-5 contained no titanium. Accordingly, although the bulk analysis of the product shows titanium to be present, it is clear that it is present in a form not having an X-ray pattern characteristic of ZSM-5.

EXAMPLE 20

(a) TASO-20, as referred to in example 1, was subjected to x-ray analysis. TASO-20 was determined to have a characteristic x-ray powder diffraction pattern which contains at least the d-spacings set forth in Table XVIII below:

TABLE XVII

| 2Θ | d, (Å) | 100 × I/Io |
|---|---|---|
| 7.6* | 11.63 | 5 |
| 11.1* | 7.97 | 12 |
| 14.0 | 6.33 | 41 |
| 19.8 | 4.48 | 35 |
| 24.3 | 3.66 | 100 |
| 28.1 | 3.175 | 17 |
| 31.6 | 2.831 | 12 |
| 34.6 | 2.592 | 22 |
| 37.6* | 2.392 | 5 |
| 40.3 | 2.238 | 6 |
| 42.8 | 2.113 | 9 |
| 46.6 | 1.949 | 4 |
| 47.6 | 1.910 | 10 |
| 52.1 | 1.755 | 12 |

*Impurity Peak (b) All of the as-synthesized TASO-20 compositions for which X-ray powder diffraction data have been obtained to date have patterns which are characterized by the data of Table XIV, below:

TABLE XVIII

| 2Θ | d, (Å) | Relative Intensity |
|---|---|---|
| 13.9–14.1 | 6.37–6.28 | m |
| 19.8–20.0 | 4.48–4.44 | m |
| 24.3–24.6 | 3.66–3.62 | vs |
| 28.1–28.2 | 3.175–3.164 | w |
| 31.5–31.7 | 2.840–2.823 | w |
| 34.6–34.7 | 2.592–2.585 | w |

(c) A portion of the as-synthesized TASO-20 of part (a) was calcined in air at 500° C. for about one hour. The calcined product was characterized by the X-ray powder diffraction pattern of Table XV below:

TABLE XIX

| 2Θ | d, (Å) | 100 × I/Io |
|---|---|---|
| 14.0 | 6.33 | 51 |
| 19.9 | 4.46 | 33 |
| 24.4 | 3.65 | 100 |
| 28.1 | 3.175 | 13 |
| 31.6 | 2.831 | 12 |
| 34.7 | 2.585 | 19 |
| 37.6* | 2.392 | 2 |
| 40.3 | 2.238 | 5 |
| 42.8 | 2.113 | 7 |
| 47.6 | 1.910 | 6 |
| 52.0 | 1.759 | 11 |

*Impurity Peak (d) The TASO-20 compositions for which X-ray powder diffraction data have been obtained to date have patterns which are characterized by the X-ray powder diffraction pattern shown in Table XVI below:

TABLE XX

| 2Θ | d, (Å) | 100 × I/Io |
|---|---|---|
| 13.9–14.1 | 6.37–6.28 | 40–51 |
| 19.8–20.0 | 4.48–4.44 | 30–40 |
| 24.3–24.6 | 3.66–3.62 | 100 |
| 28.1–28.2 | 3.175–3.164 | 13–18 |
| 31.5–31.7 | 2.840–2.823 | 12–15 |
| 34.6–34.7 | 2.592–2.585 | 15–22 |
| 40.2–40.3 | 2.243–2.238 | 4–6 |
| 42.7–42.9 | 2.118–2.108 | 5–9 |
| 47.5–47.6 | 1.914–1.910 | 6–11 |
| 52.0–52.2 | 1.759–1.752 | 10–12 |

PROCESS APPLICATIONS

The TASO compositions of this invention have unique surface characteristics making them useful as molecular sieves and as catalyst or as bases for catalysts in a variety of separation, hydrocarbon conversion and oxidative combustion processes. The TASO composition can be impregnated or otherwise associated with catalytically active metals by the numerous methods known in the art and used, for example, in fabricating catalysts compositions containing alumina or aluminosilicate materials.

TASO's may be employed for separating molecular species in admixture with molecular species of a different degree of polarity or having different kinetic diameters by contacting such mixtures with a TASO(s) having pore diameters large enough to absorb at least one but not all molecular species of the mixture based on the polarity of the adsorbed molecular species and/or its kinetic diameter. When TASOs are employed for such separation processes the TASOs are at least partially activated whereby some molecular species selectively enter the intracrystalline pore system thereof.

The hydrocarbon conversion reactions catalyzed by TASO compositions include; cracking, hydrocracking; alkylation of both the aromatic and isoparaffin types; isomerization (including xylene isomerization); pollymerization; reforming; hydrogenation; dehydrogenation; transalkylation; dealkylation; and hydration.

When a TASO containing catalyst compositions contains a hydrogenation promoter, such promoter may be platinum, palladium, tungsten, nickel or molybdenum and may be used to treat various petroleum stocks including heavy petroleum residual stocks, cyclic stocks and other hydrocrackable charge stocks. These stocks can be hydocracked at temperatures in the range of between about 400° F. and about 825° F. using molar ratios of hydrogen to hydrocarbon in the range of between about 2 and about 80, pressures between about 10 and about 3500 p.s.i.g., and a liquid hourly space velocity (LHSV) of between about 0.1 and about 20, preferably between about 1.0 and about 10.

TASO containing catalyst compositions may also be employed in reforming processes in which the hydrocarbon feedstocks contact the catalyst at temperatures between about 700° F. and about 1000° F., hydrogen pressures of between about 100 and about 500 p.s.i.g., LHSV values in the range between about 0.1 and about 10 and hydrogen to hydrocarbon molar ratios in the range between about 1 and about 20, preferably between about 4 and about 12.

Further, TASO containing catalysts which contain hydrogenation promoters, are also useful in hydroisomerization processes wherein the feedstock(s), such as normal paraffins, is converted to saturated branchedchain isomers. Hydroisomerization processes are typically carried out at a temperature between about 200° F. and about 600° F., preferably between about 300° F. and about 550° F. with an LHSV value between about 0.2 and about 1.0. Hydrogen is typically supplied to the reactor in admixture with the hydrocarbon feedstock in molar proportions of hydrogen to the feedstock of between about 1 and about 5.

TASO-containing compositions similar to those employed for hydrocracking and hydroisomerization may also be employed at between about 650° F. and about 1000° F., preferably between about 850° F. and about 950° F. and usually at somewhat lower pressures within the range between about 15 and about 50 p.s.i.g. for the hydroisomerization of normal paraffins. Preferably the paraffin feedstock comprises normal paraffins having a carbon number range of $C_7$–$C_{20}$. The contact time between the feedstock and the TASO containing catalyst is generally relatively short to avoid undesirable side reactions such as olefin polymerization and paraffin cracking. LHSV values in the range between about 0.1 and about 10, preferably between about 1.0 and about 6.0 are suitable.

The low alkali metal content (often not measurable by current analytical techniques) of the instant TASO compositions make them particularly well suited for use in the conversion of alkylaromatic compounds, particularly for use in the catalytic disproportionation of toluene, xylene, trimethylbenzenes, tetramethylbenzenes and the like. In such disproportionation processes it has been observed that isomeration and transalkylation can also occur. The TASO-containing catalysts for such processes will typically include Group VIII noble metal adjuvants alone or in conjunction with Group VI-B metals such as tungsten, molybdenum and chromium which are preferably included in such catalyst compositions in amounts between about 3 and about 15 weight-% of the overall catalyst composition. Extraneous hydrogen can, but need not be present in the reaction zone which is maintained at a temperature between about 400° and about 750° F., pressures in the range between about 100 and about 2000 p.s.i.g. and LHSV values in the range between about 0.1 and about 15.

TASO containing catalysts may be employed in catalytic cracking processes wherein such are preferably employed with feedstocks such as gas oil, heavy naphthas, deasphalted crude oil residues etc. with gasoline being the principal desired product. Temperature conditions are typically between about 850° and about 1100° F., LHSV values between about 0.5 and about 10 pressure conditions are between about 0 p.s.i.g. and about 50 p.s.i.g.

TASO containing catalysts may be employed for dehydrocyclization reactions which employ paraffinic hydrocarbon feedstocks, preferably normal paraffins having more than 6 carbon atoms, to form benzene, xylenes, toluene and the like. Dehydrocyclization processes are typically carried out using reaction conditions similar to those employed for catalytic cracking. For such processes it is preferred to use a Group VIII non-noble metal cation such as cobalt and nickel in conjunction with the TASO composition.

TASO containing catalysts may be employed in catalytic dealkylation where paraffinic side chains are cleaved from aromatic nuclei without substantially hydrogenating the ring structure at relatively high temperatures in the range between about 800° F. and about 1000° F. at moderate hydrogen pressures between about 300 and about 1000 p.s.i.g. with other conditions being similar to those described above for catalytic hydrocracking. TASO containing catalysts for catalytic dealkylation are of the same type described above in connection with catalytic dehydrocyclization. Particularly desirable dealkylation reactions contemplated herein include the conversion of methylnaphthalene to naphthalene and toluene and/or xylenes to benzene.

TASO containing catalysts may be used in catalytic hydrofining wherein the primary objective is to provide for the selective hydrodecomposition of organic sulfur and/or nitrogen compounds without substantially affecting hydrocarbon molecules present therewith. For this purpose it is preferred to employ the same general conditions described above for catalytic hydrocracking. The catalysts as the same typically of the same general nature as described in connection with dehydrocyclization generations. Feedstocks commonly employed for catalytic hydroforming include: gasoline fractions; kerosenes; jet fuel fractions; diesel fractions; light and heavy gas oils; deasphalted crude oil residua; and the like. The feedstock may contain up to about 5 weight-percent of sulfur and up to about 3 weight-percent of nitrogen.

TASO containing catalysts may be employed for isomerization processes under conditions similar to those described above for reforming although isomerization processes tend to require somewhat more acidic catalysts than those employed in reforming processes. Olefins are preferably isomerized at temperatures between about 500° F. and about 900° F., while paraffins, naphthenes and alkyl aromatics are isomerized at temperatures between about 700° F. and about 1000° F. Particularly desirable isomerization reactions contemplated herein include the conversion of n-heptane and/or n-octane or isoheptanes, iso-octanes, butane to isobutane, methylcyclopentane to cylcohexane, meta-xylene and/or ortho-xylene to para-xylene, 1-butene to 2-butene and/or isobutene, n-hexene to isohexane, cyclohexane to methylcyclopentene etc. The preferred cation form is a combination of a TASO with polyvalent metal compounds (such as sulfides) of metals of Group II-A, Group II-B and rare earth metals. For alkylation and dealkylation processes TASO compositions having pores of at least 5A are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In alkylation of benzene, toluene and xylene, the preferred alkylation agents are olefins such as ethylene and propylene.

The TASO compositions of this invention may be employed in conventional molecular sieving processes as heretofore have been carried out using aluminosilicate, aluminophosphate or other commonly employed molecular sieves. TASO compositions are preferably activated prior to their use in a molecular sieve process to remove any molecular species which may be present in the intracrystalline pore system as a result of synthesis or otherwise. For the TASO compositions this is sometimes accomplished by thermally destroying the organic species present in an as-synthesized TASO since such organic species may be too large to be desorbed by conventional means.

The TASO compositions of this invention are also useful as adsorbents and are capable of separating mixtures of molecular species both on the basis of molecular size (kinetic diameters) and based on the degree of polarity of the molecular species. When the separation of molecular species is based upon the selective adsorption based on molecular size, the TASO is chosen in view of the dimensions of its pores such that at least the smallest molecular specie of the mixture can enter the intracrystalline void space while at least the largest specie is excluded. When the separation is based on degree of polarity it is generally the case that the more hydrophilic TASO will preferentially adsorb the more polar molecular species of a mixture having different degrees of polarity even though both molecular species can communicate with the pore system of the TASO.

The instant TASO compositions may be further characterized and distinguished from aluminophosphates by reference to the catalytic properties exhibited by the TASO compositions. When the TASO compositions are tested for n-butane cracking and compared with aluminophosphate compositions having a similar topology it has been observed that the TASO compositions are more active catalysts as indicated by a higher numerical value for n-butane cracking.

What is claimed is:

1. Process for converting a hydrocarbon which comprises contacting said hydrocarbon under hydrocarbon converting conditions with a crystalline molecular sieve comprising at least one composition selected from crystalline molecular sieves having chemical compositions in the anhydrous form represented by the unit empirical formula $$mR:(Ti_xAl_ySi_z)O_2$$

wherein "R" represents at least one organic templating agent present in the intracrystalline pore system; "m" represents the moles of "R" present per mole of $(Ti_xAl_ySi_z)O_2$ and has a value of from zero to about 0.3; and "x", "y" and "z" represent the mole fractions of titanium, aluminum and silicon, respectively, present as tetrahedral oxides, said mole fractions being such that they are within the compositional area defined by points A, B, C and D of FIG. 1 and having a characteristic x-ray powder diffraction pattern selected from the group consisting of Tables V, VII, XI and XVIII.

2. Process according to claim 1 wherein the hydrocarbon conversion process is isomerization.

3. Process according to claim 1 wherein said compositional area is defined by points A, B, D, E and F of FIG. 1.

4. Process according to claim 1 wherein said compositional area is defined by points a, b and c of FIG. 2.

5. Process according to claim 1 wherein said at least one composition comprises at least one molecular sieve selected from the group consisting of TASO-20, TASO-38, TASO-48 and TASO-49.

6. Process according to claim 1, wherein said at least one composition comprises TASO-48.

7. Process according to claim 1 wherein said hydrocarbon conversion process is hydroisomerization and said molecular sieve is included in a catalyst which further comprises a hydrogenation promoter.

8. Process according to claim 7 wherein said hydrocarbon conversion process is hydroisomerization and said molecular sieve is included in a catalyst which further comprises a hydrogenation promoter.

9. Process according to claim 1 wherein said process is hydrofining and said molecular sieve is included in a catalyst which further comprises a non-noble Group VIII metal cation.

10. Process according to claim 1 wherein the hydrocarbon conversion process is catalytic dealkylation and said molecular sieve is included in a catalyst which further comprises a hydrogenation promoter.

11. Process according to claim 10 wherein said hydrogenation promoter is platinum, palladium, tungsten, nickel or molybdenum.

12. Process according to claim 10 wherein said composition has pores of at least 5 Angstroms.

* * * * *